United States Patent [19]

Jones

[11] 4,056,982

[45] Nov. 8, 1977

[54] APPARATUS AND METHOD FOR SAMPLING A LIQUID

[76] Inventor: Richard Warren Jones, 26 Bucknell Rd., Bicester, Oxon, England

[21] Appl. No.: 749,990

[22] Filed: Dec. 13, 1976

[30] Foreign Application Priority Data

Dec. 19, 1975 United Kingdom .............. 52233/75

[51] Int. Cl.$^2$ ........................................... G01N 1/14
[52] U.S. Cl. ............................................. 73/421 B
[58] Field of Search ............................. 73/421 B, 422

[56] References Cited

U.S. PATENT DOCUMENTS 3,015,957  1/1962  Paulson .............................. 73/421 B
3,771,366  11/1973  Tholin ................................ 73/421 B

FOREIGN PATENT DOCUMENTS 1,360,346  7/1974  United Kingdom .............. 73/421 B Primary Examiner—S. Clement Swisher
Attorney, Agent, or Firm—Brisebois & Kruger

[57] ABSTRACT

An apparatus for sampling a liquid includes a chamber into which liquid is pumped and a pressure sensor that detects the time instant when liquid reaches a sample duct from the container. The pump is controlled by a signal from a timing device that is initiated by the pressure sensor so that the volume of liquid being pumped through the sample duct can be controlled by the timing device switching off the pump. The pump is started at predetermined time intervals by a periodic timer. After the pump is switched off, the chamber is drained of liquid and reoccupied by air.

12 Claims, 2 Drawing Figures

APPARATUS AND METHOD FOR SAMPLING A
LIQUID

BACKGROUND OF THE INVENTION

The invention relates to apparatus and a method for periodically sampling a liquid and particularly to sampling wastewaters.

The purpose of sampling a liquid is to obtain a representative portion of the liquid from which its average composition can be determined. When sampling a flowing liquid, its average composition over a specific period of time is required (for example, a 24 hour average). This is normally done by compositing a set of individual sub-samples taken with sufficient frequency to include all the effects of changes in composition of the flow during the period of the sample. The more frequent the taking of these individual samples, the more representative will be the complete sample.

The frequency of the sampling may be at regular time intervals or at time intervals in inverse proportion to the rate of flow of the sampled liquid. The latter case being flow-proportional sampling.

The individual sub-samples may be composited in a single container to give a gross average or alternatively, may be distributed into an array of separate containers to aportion the flow from hour to hour.

When sampling wastewaters it is important to include any solids waste that is being carried by the water. Wastewaters normally flow along open channels or ventilated drains and samples of this liquid are usually obtained by pumping a small volume into one or more containers at predetermined time intervals. Wastewaters often contain settleable particulate matter like washings and grit and also contain fine solids matter in suspension within the liquid. To obtain a representative sample of these solids, the wastewater must be pumped at high velocity, to prevent the settleable matter from being left behind, and be transported through tubing of sufficient bore to avoid the risk of internal blockage within the sampling apparatus.

Wastewaters may also contain solids matter in the form of debris like rags, leaves and other coarse material which is not normally required to be included in the sample. These solids must not be allowed to obstruct the inlet or the internal parts of the sampling apparatus.

Sampling apparatus for wastewaters have hitherto been based on powerful pumps delivering large individual samples through large bore delivery tubes. However, if the total sample volume is much over one gallon, the sample becomes difficult to carry and therefore most practical sampling devices have a limited capacity of about one gallon. So if the individual samples are of large volume, then the frequency of these samples must be correspondingly low and so the accuracy of the total sample may also be low.

SUMMARY OF THE INVENTION

According to the present invention there is provided apparatus for and a method of sampling a liquid. The apparatus for sampling a liquid comprising:

a housing having an inlet for liquid to be sampled and an outlet for a sample;

a displacer of liquid in the housing linking the inlet to an entry to a working chamber;

the working chamber having a plenum of sectional area such that liquid being displaced into the working chamber through the entry is reduced in velocity and enabled to form a uniform rising surface;

drive means for the displacer which, in a first state, cause the displacer to drive liquid from the inlet into the chamber by way of the entry and, in a second state cause the displacer to allow liquid in the working chamber to pass from the entry to the inlet;

a sample duct joining the outlet to a sample tube projecting into the plenum, the sample tube defining an opening disposed in an opposite direction to the upward direction of movement of a free surface of liquid displaced through the entry into the working chamber by the displacer with the drive means in the first state, the opening being sized such that a sensible pressure increase is created within the container when displaced liquid obturates the opening;

a sensor for detecting pressure changes in the plenum; and switch means linking the sensor to the drive means so that on the sensor detecting a pressure increase in the plenum due to obturation of the sample duct by a liquid surface the drive means is subsequently caused to switch from the first state to the second.

The method of sampling a liquid comprising the steps of:

pumping a liquid into a chamber to provide in the chamber a rising free surface of the liquid acting to displace air or other gas in the chamber through a tube projecting towards the rising surface in the chamber;

allowing the rising liquid to enter and so close the tube end;

sizing the entry to the tube end such that a flow of liquid therein creates a sensible pressure rise within the chamber;

conveying liquid in the tube out of the chamber to provide a sample;

ceasing to pump the liquid after a predetermined time interval following the pressure rise within the chamber; and thereafter allowing residual liquid in the tube to fall back into the chamber and liquid in the chamber to fall, under the action of gravity, out of the chamber.

It is an object of this invention to provide a means of obtaining liquid and wastewater samples in small volumes from a liquid periodically flowing at high velocity through tubing of large bore.

Other objects of this invention will be apparent hereinafter from the specification and from the recital of the appended claims, particularly when read in conjunction with the accompanying drawings.

DESCRIPTION OF THE PREFERRED EMBODIMENTS

Figure 1:
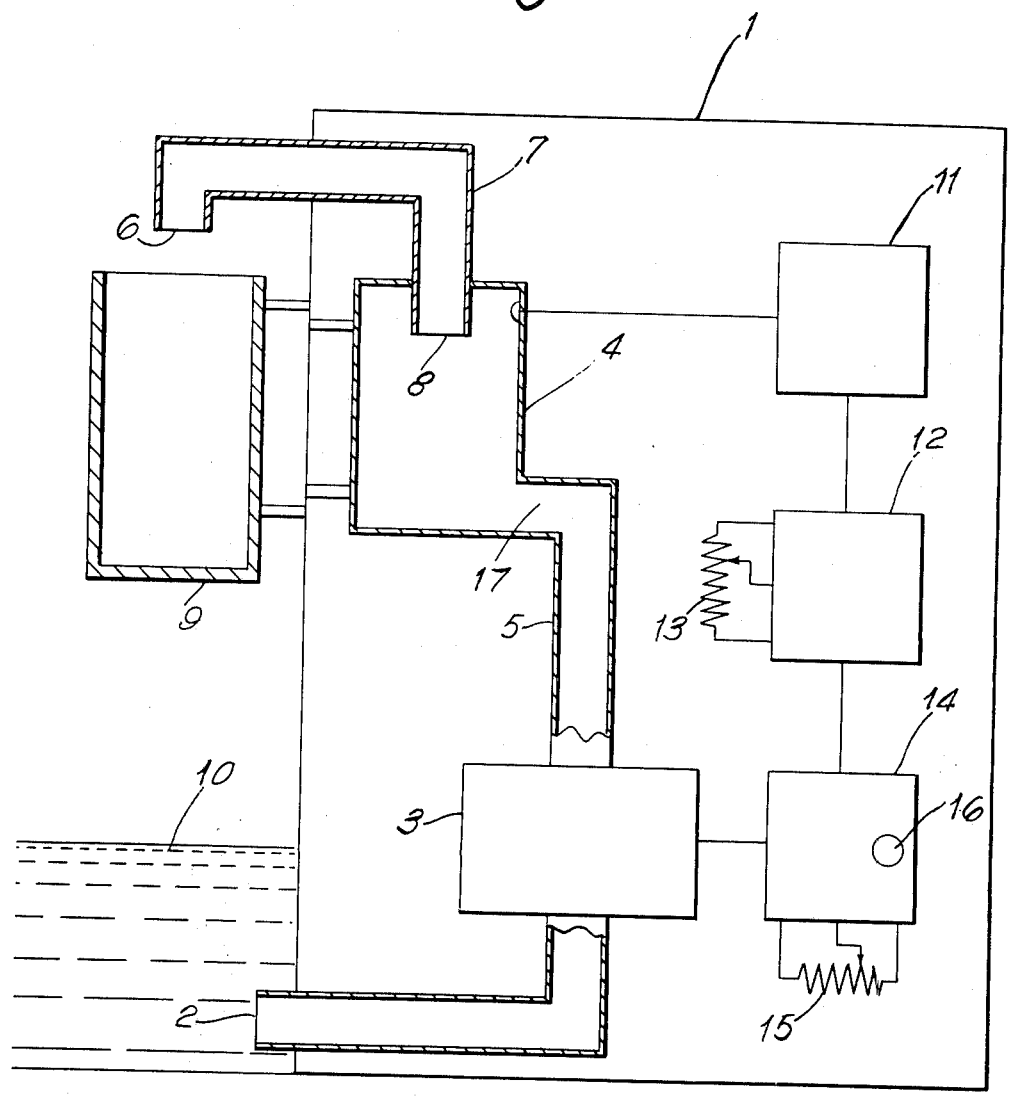
FIG. 1 is a schematic diagram illustrating the arrangement of components of a sampling apparatus made in accordance with this invention.

FIG. 1 shows a housing 1 with an inlet 2 leading to a displacer 3. A delivery tube 5 communicates the displacer to a working chamber 4 fixed to the housing. The working chamber 4 leading to the outlet 6 through a sample duct 7 which protrudes into the working chamber and has an opening 8 with an axis in a generally vertical attitude. Outlet 6 is positioned above a collection vessel 9 fixed to the housing 1. Inlet 2 is immersed in the liquid 10 to be sampled. A pressure sensor 11 detects the pressure within the working chamber 4 and can communicate a signal to switching means 12 when a sensible pressure rise occurs within the working chamber. The switching means 12 encorporates a timing device 13 to delay the transmission of a switching signal to drive means 14. Drive means 14, encorporates a periodic timer 15 which intermittently operates the displacer 3. Switching means 12 interrupts the driving of the displacer 3 and re-sets the periodic timer 15. Switch 16 switches the apparatus on or off.

When switch 16 is put into the "on" position the periodic timer 15 operates the drive means 14 after a predetermined time period. This causes displacer 3 to operate in its first state and draw liquid 10 in through the inlet 2 and force it through delivery tube 5 into the working chamber 4 through entry 17, where it forms, without splashing, a rising uniform surface within the working chamber and displaces air out through delivery duct 7. When the liquid surfaces reaches the opening 8, liquid flows into the sample duct 7. Because liquid has a higher viscosity and density than air, the acceleration of the liquid into the sample duct 7 creates a pronounced increase in pressure within the working chamber. This causes pressure sensor 11 to send a signal to switching means 12. After a predetermined time delay set by timing device 13 a second signal is sent from the switching means to the drive means 3 causing the drive means to change from its first state to operate in its second state and operate the displacer to drive liquid from the working chamber entry 17 backwards to the inlet 2, thereby emptying sample duct 7 and working chamber 4. During the predetermined time delay, a predetermined volume of liquid is being forced through sample duct 7 into the collection vessel 9. This volume of liquid is an individual sample.

This series of operations is repeated cyclically by the periodic timer 15 to produce a set of individual samples over a period of time to form a composite sample within the collection vessel 9.

Figure 2:
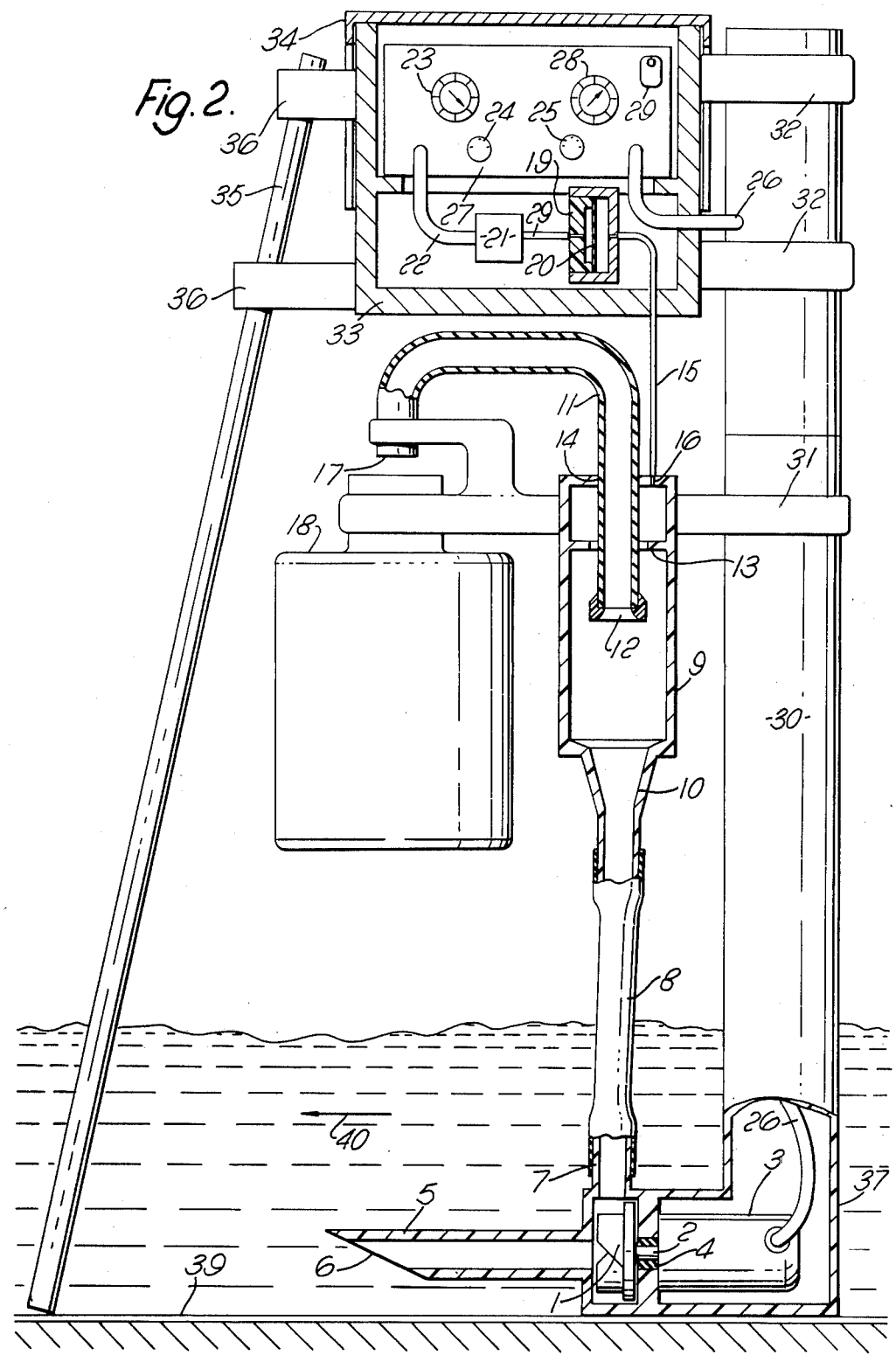
FIG. 2 is an elevational view, partly broken away and sectioned, of a sampling apparatus made in accordance with an embodiment of this invention.

Referring to FIG. 2 of the drawings, the apparatus of this embodiment of the invention, which is intended mainly for sampling from open channels, stands on a floor 39 of a channel. The apparatus has a vertical pump housing 30 and a pair of rigid legs 35 (only one shown) forming a self supporting tripod. The two legs 35 are secured to a rigid frame 33 by four leg struts 36. The pump housing 30 is attached to the rigid frame by two brackets 32. To protect the contents of the frame 33 from the environment a weatherproof cover 34 encloses the frame. A supporting member 31 rigidly locates a working chamber 9, an outlet 17 of a sample duct 11 and locates a sample collection vessel 18. The channel contains a liquid flowing in a direction indicated by arrow 40.

An inlet opening 6, angled to the flow direction, faces downstream to avoid any debris adhering to the inlet. The length of an inlet tube 5 locates the opening 6 at a distance from the heel 37 of the housing 30 so that any elongate debris that may be present in the liquid and may collect on the heel 37 will not usually be long enough to trail alongside and be drawn into the opening 6.

A two bladed centrifugal impeller 1 mounted on a stainless steel shaft 2 is driven by a low voltage electric motor 3. A seal 4 prevents liquid entering the motor 3 and pump housing 30. A pump outlet 7 leads through a delivery tube 8 to the working chamber 9 having a diffusing section 10, a splash ring 13 and an opening 14. A flexible sample duct 11 forms an airtight fit within opening 14 and extends below splash ring 13. A bellmouth piece 12 fits onto the inlet of the sample duct 11; an outlet 17 to the sample duct being held over the neck of a collection vessel 18 by the supporting member 31.

An air tube 15 leads from an aperture 16 in the top of the working chamber 9 to diaphragm chamber 19 to isolate the damp air within the working chamber from a pressure switch 21. Damp air can adversly affect electric pressure switches. The diaphragm chamber 19, which can be opened to clean out any condensate, contains a flexible diaphragm 20 through which pressure changes are freely communicated to the pressure switch 21. Such pressure changes close electric contacts within the pressure switch thereby signalling electronically the pressure change through a cable 22 to control box 27.

The control box 27 contains a periodic secondary timer (not shown) linked to a control knob 28 for switching on the motor 3 at predetermined time intervals that can be preset from one minute to sixty minutes. A knob 23 is linked to a primary timer (not shown) to control the time interval between the signal from pressure switch 21 and the switching off of the electric motor 3. Socket 24 enables the periodic timer (secondary) to be externally governed by a sensor monitoring the flow rate of liquid within the channel so that the frequency of sampling is in proportion to the flow rate. Socket 25 is a power input socket for a battery cable (not shown). A cable 26 supplies power to the electric motor 3. An on-off switch 29 controls the supply of electrical power to the primary and secondary timers.

When a sample of the flow is required switch 29 is put in the ON position thereby activating the secondary timer. After the period of time preset by sample interval knob 28 power is switched through the cable 26 to the motor 3 which rotates the centrifugal impeller 1 at high speed forcing liquid up through delivery pipe 8 into the diffusing section 10 of the working chamber 9. Diffusing section 10 reduces the velocity of inflowing liquid to avoid spurious obturation of the inlet 12 by liquid splashing onto that inlet. Splash ring 13 inhibits liquid reaching the aperture 16 at the top of the working chamber. The continuing inflow of liquid causes a liquid surface to rise until it reaches the bell mouth opening 12. Liquid then obturates the opening preventing air from leaving the working chamber. The higher viscosity and density of the flowing liquid creates an increase in pressure in air trapped above the free surface of liquid within the working chamber 9.

This increase in pressure is transmitted through aperture 16 and tube 15 to diaphragm chamber 19 causing the diaphragm 20 to deflect and thereby communicating the pressure through tube 29 to the pressure switch 21. Electrical contact within switch 21 signals the primary timer within the control box 27 through cable 22. After a small time interval predetermined by the setting of control knob 23, the power to motor 3 is switched off and the secondary timer is reset. During this primary time interval the pump impeller 1 has been forcing liquid through the sample duct 11 into the collection vessel 18. When the impeller 1 stops rotating the pumped liquid decelerates and then flows backwards under gravity returning through sample duct 11, down through working chamber 9, delivery tube 8 and out through the intake 5.

All the liquid that has passed sample duct opening 17 will be retained in the collection vessel. The remainder of the pumped liquid will have flowed out through inlet 6 thereby dislodging any debris that may have been attracted to the inlet opening. A small volume of liquid will remain within the pump because the pump is submersed beneath the flow surface. This sequence of events is repeated cyclically by time intervals predetermined by the setting of control knob 28.

A portable version of the embodiment of the invention has in its construction an anodised aluminium alloy for the legs 35, leg struts 36, frame 33 and cover 34. The pump housing 30, brackets 31, working chamber 9 and bottle 18 are made from polypropylene. Both aluminium alloy and polypropylene are reasonably resistant to adverse environments.

A 12 volt permanent magnet DC motor of 20 watts power drives the impeller 1 at 4500 rpm to deliver about 250 cubic centimeters per second of liquid through delivery pipe 8. The bore diameter of the delivery pipe 8 being 12 millimeters and of the sample duct being 10 millimeters. Collection vessel 18 has a capacity of 5000 cubic centimeters.

Solid state integrated circuits are used for the primary and secondary timers and these control the power to the motor 3 through a Darlington-type power transistor switch.

A 12 volt sealed lead gel rechargeable battery of 4.5 Ampere hour capacity is used to supply power to the timers (0.008 amperes — continuous) and the motor (1.7 amperes — intermittent). The time taken for the motor to complete a sampling cycle is typically less than 3 seconds so that small 4.5 ampere hour batteries can give over 2500 individual samples. Sample interval knob 28 has ten settings ranging from 1 sample per minute to 1 sample per 60 minutes. The settings for control knob 23 are graduated in terms of cubic centimeters of liquid delivered through opening 17 on each operation of motor 3 rather than in terms of time delay on switching off the motor. To avoid continuous running of the motor 3 when liquid level in the channel falls below the inlet 6, the motor is switched on for a limited period of only 6 seconds on each cycle of the secondary timer.

What is claimed is:
1. Apparatus for sampling a liquid comprising,
   i. a housing having an inlet for liquid to be sampled and an outlet for a sample;
   ii. a displacer of liquid in the housing linking the inlet to an entry to a working chamber;
   iii. the working chamber having plenum of a sectional area such that liquid being displaced into the working chamber through the entry is reduced in velocity and enabled to form a uniform rising surface;
   iv. drive means for the displacer which, in a first state, causes the displacer to drive liquid from the inlet into the chamber by way of the entry and, in a second state causes the displacer to allow liquid in the working chamber to pass from the entry to the inlet;
   v. a sample duct joining the outlet to a sample tube projecting into the plenum, the sample tube defining an opening disposed in an opposite direction to the upward direction of movement of a free surface of liquid displaced through the entry into the working chamber by the displacer with the drive means in the first state, the opening being sized such that a sensible pressure increase is created within the container when displaced liquid obturates the opening;
   vi. a sensor for detecting pressure changes in the plenum; and
   vii. switch means linking the sensor to the drive means so that on the sensor detecting a pressure increase in the plenum due to obturation of the sample duct by a liquid surface the drive means is subsequently caused to switch from the first state to the second.

2. Apparatus as claimed in claim 1 wherein the switch means includes a primary timer so that the drive means is caused to switch from the first state to the second a predetermined time after the pressure sensor detects a pressure increase.

3. Apparatus as claimed in claim 2 wherein the switch means includes a secondary timer so that a predetermined time after the drive means is caused to switch from the first state to the second the drive means is caused to switch back to the first state from the second.

4. Apparatus as claimed in claim 3 wherein the switch means includes an automatic recycling control so that the switching of drive means between first and second states and between second and first states is repeated cyclically.

5. Apparatus as claimed in claim 4 including flow rate sensing means to enable the cyclic repetition of switching of drive means to be varied at a rate dependent on the flow rate of liquid in the vicinity of the inlet.

6. Apparatus as claimed in claim 1 wherein the displacer is a centrifugal pump.

7. Apparatus as claimed in claim 1 wherein the drive means is an electric motor.

8. Apparatus as claimed in claim 1 wherein the sample tube opens into the plenum by way of a bell-mouth.

9. Apparatus as claimed in claim 1 wherein the pressure sensor communicates with the working chamber through a diaphragm across which pressure is freely transmitted, the diaphragm being impervious to moisture.

10. Apparatus as claimed in claim 1 including a collection vessel for a sample dispensed from the outlet.

11. Apparatus as claimed in claim 1 including a series of collection vessels automatically displaceable at predetermined periods to enable sets of samples dispensed from the outlet to be collected separately.

12. A method of sampling a liquid comprising the steps of:
   i. pumping a liquid into a chamber to provide in the chamber a rising free surface of the liquid acting to displace air or other gas in the chamber through a tube projecting towards the rising surface in the chamber;
   ii. allowing the rising liquid to enter and so close the tube end;
   iii. sizing the entry to the tube end such that a flow of liquid therein creates a sensible pressure rise within the chamber;
   iv. conveying liquid in the tube out of the chamber to provide a sample;
   v. ceasing to pump the liquid after a predetermined time interval following the pressure rise within the chamber; and,
   vi. thereafter allowing residual liquid in the tube to fall back into the chamber and liquid in the chamber to fall, under the action of gravity, out of the chamber.

* * * * *